(12) United States Patent
Lim et al.

(10) Patent No.: US 7,981,244 B2
(45) Date of Patent: Jul. 19, 2011

(54) CATHETER BALLOON HAVING IMPREGNATED BALLOON SKIRT SECTIONS

(75) Inventors: Florencia Lim, Union City, CA (US); Jeong S Lee, Diamond Bar, CA (US); Edwin Wang, Tustin, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1140 days.

(21) Appl. No.: 11/585,071

(22) Filed: Oct. 23, 2006

(65) Prior Publication Data

US 2007/0038240 A1 Feb. 15, 2007

Related U.S. Application Data

(62) Division of application No. 10/200,274, filed on Jul. 22, 2002, now Pat. No. 7,147,619.

(51) Int. Cl.
*B29C 65/00* (2006.01)
*B32B 37/00* (2006.01)

(52) U.S. Cl. ............... 156/308.2; 156/294; 604/96.01; 604/103; 606/194

(58) Field of Classification Search ............. 156/292, 156/293, 294, 308.2, 308.4, 309.6; 604/96.01, 604/103, 103.05, 103.06; 606/191, 192, 606/194
See application file for complete search history.

(56) References Cited

U.S. PATENT DOCUMENTS

| | | | |
|---|---|---|---|
| 4,003,382 A * | 1/1977 | Dyke | 604/103 |
| 5,195,969 A | 3/1993 | Wang et al. | |
| 5,290,306 A | 3/1994 | Trotta et al. | |
| 5,374,473 A | 12/1994 | Knox et al. | |
| 5,788,626 A | 8/1998 | Thompson | |
| 5,868,704 A | 2/1999 | Campbell et al. | |
| 6,016,848 A | 1/2000 | Egres, Jr. | |
| 6,086,556 A | 7/2000 | Hamilton et al. | |
| 6,110,333 A * | 8/2000 | Spethmann et al. | 204/252 |
| 6,120,477 A | 9/2000 | Campbell et al. | |
| 6,306,144 B1 * | 10/2001 | Sydney et al. | 606/108 |
| 6,428,506 B1 | 8/2002 | Simhambhatla et al. | |
| 6,699,170 B1 * | 3/2004 | Crocker et al. | 600/3 |
| 6,946,173 B2 * | 9/2005 | Lim et al. | 428/35.2 |
| 2002/0146557 A1 * | 10/2002 | Claude et al. | 428/336 |
| 2003/0180488 A1 | 9/2003 | Lim et al. | |

FOREIGN PATENT DOCUMENTS

| WO | WO 95/05555 | 2/1995 |
|---|---|---|
| WO | WO 97/02791 | 1/1997 |

* cited by examiner

*Primary Examiner* — John L Goff
(74) *Attorney, Agent, or Firm* — Fulwider Patton LLP; Thomas H. Majcher, Esq.

(57) ABSTRACT

A balloon catheter and a method of making a balloon catheter, having a balloon with a first layer and a second layer, the first layer having at least one impregnated section impregnated with a polymeric material compatible with a polymeric material forming the catheter shaft. At least a portion of the impregnated section is fusion bonded to the shaft. In a presently preferred embodiment, the impregnated section is adjacent to a section of the first layer which is not impregnated with the compatible polymeric material. The impregnated section provides improved bonding of the balloon to the catheter shaft while minimizing the effect of the bond on catheter performance characteristics such as profile and flexibility.

12 Claims, 2 Drawing Sheets

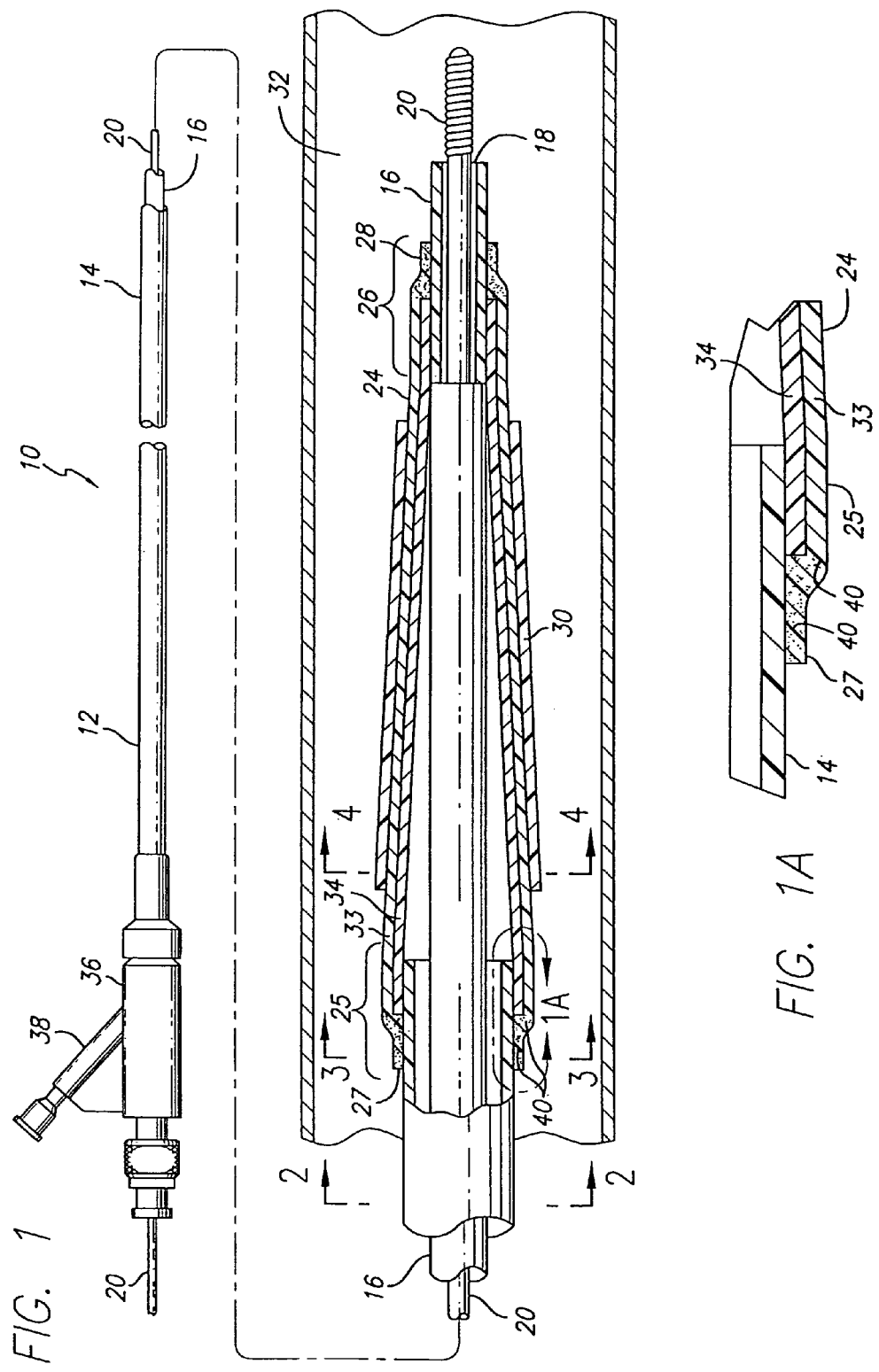

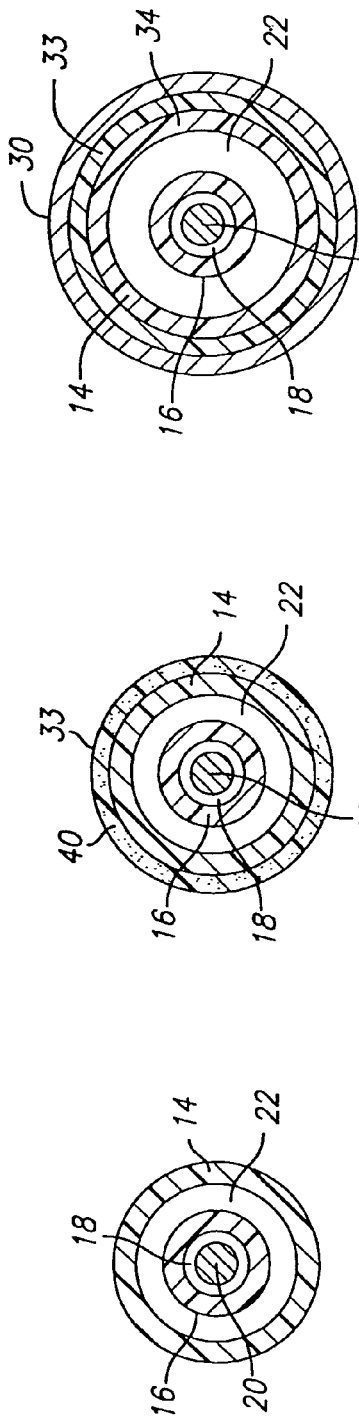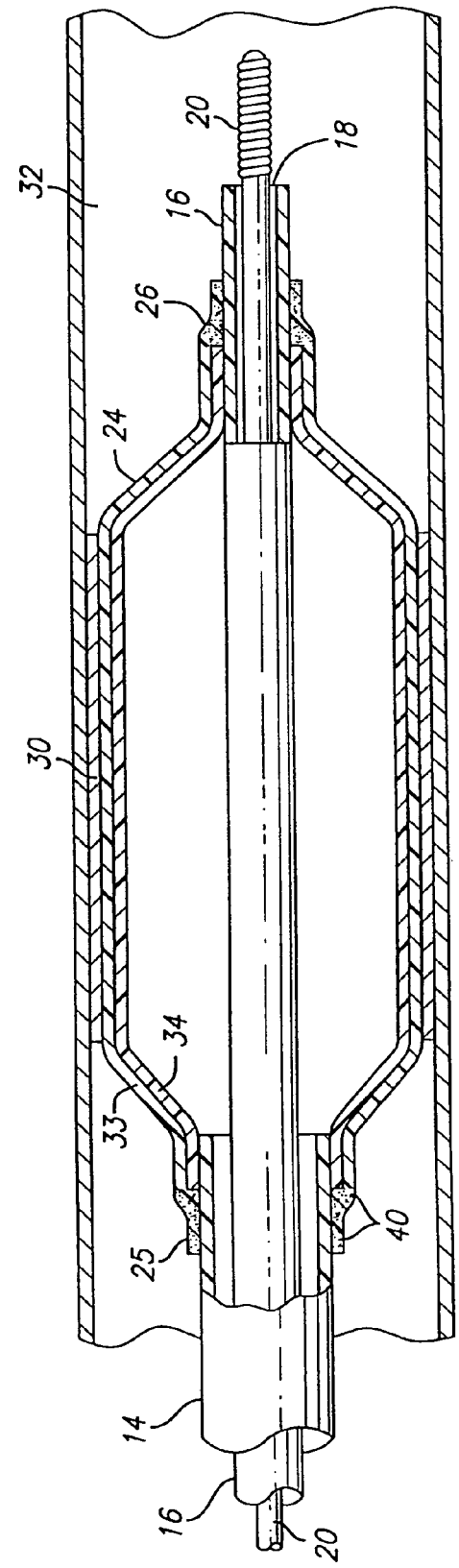

CATHETER BALLOON HAVING IMPREGNATED BALLOON SKIRT SECTIONS

This application is a division of U.S. patent application Ser. No. 10/200,274, filed Jul. 22, 2002, issued Dec. 12, 2006, U.S. Pat. No. 7,147,619.

BACKGROUND OF THE INVENTION

This invention generally relates to medical devices, and particularly to intracorporeal devices for therapeutic or diagnostic uses, such as balloon catheters. In percutaneous transluminal coronary angioplasty (PTCA) procedures, a guiding catheter is advanced until the distal tip of the guiding catheter is seated in the ostium of a desired coronary artery. A guidewire, positioned within an inner lumen of a dilatation catheter, is first advanced out of the distal end of the guiding catheter into the patient's coronary artery until the distal end of the guidewire crosses a lesion to be dilated. Then the dilatation catheter having an inflatable balloon on the distal portion thereof is advanced into the patient's coronary anatomy, over the previously introduced guidewire, until the balloon of the dilatation catheter is properly positioned across the lesion. Once properly positioned, the dilatation balloon is inflated with fluid one or more times to a predetermined size at relatively high pressures (e.g. greater than 8 atmospheres) so that the stenosis is compressed against the arterial wall and the wall expanded to open up the passageway. Generally, the inflated diameter of the balloon is approximately the same diameter as the native diameter of the body lumen being dilated so as to complete the dilatation but not overexpand the artery wall. Substantial, uncontrolled expansion of the balloon against the vessel wall can cause trauma to the vessel wall. After the balloon is finally deflated, blood flow resumes through the dilated artery and the dilatation catheter can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate and to strengthen the dilated area, physicians frequently implant a stent inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter and the stent left in place within the artery at the site of the dilated lesion. Stent covers on an inner or an outer surface of the stent have been used in, for example, the treatment of pseudo-aneurysms and perforated arteries, and to prevent prolapse of plaque. Similarly, vascular grafts comprising cylindrical tubes made from tissue or synthetic materials such as polyester, expanded polytetrafluoroethylene, and DACRON may be implanted in vessels to strengthen or repair the vessel, or used in an anastomosis procedure to connect vessels segments together.

In the design of catheter balloons, characteristics such as strength, compliance, and profile of the balloon are carefully tailored depending on the desired use of the balloon catheter, and the balloon material and manufacturing procedure are chosen to provide the desired balloon characteristics. A variety of polymeric materials are conventionally used in catheter balloons. Use of polymeric materials such as PET that do not stretch appreciably consequently necessitates that the balloon is formed by blow molding, and the deflated balloon material is folded around the catheter shaft in the form of wings, prior to inflation in the patient's body lumen. However, it can be desirable to employ balloons, referred to as formed-in-place balloons, that are not folded prior to inflation, but which are instead expanded to the working diameter within the patient's body lumen from a generally cylindrical or tubular shape (i.e., essentially no wings) that conforms to the catheter shaft.

A catheter balloon formed of expanded polytetrafluoroethylene (ePTFE) has been suggested. ePTFE is PTFE which has been expanded to form porous ePTFE which typically has a node and fibril microstructure comprising nodes interconnected by fibrils. However, ePTFE has proven difficult to bond to balloon liner materials and/or to catheter shafts. One difficulty has been bonding ePTFE absent the use of adhesives which can increase stiffness at the bond site, and/or bonding pretreatments which can cause decomposition of the ePTFE fibril structure.

It would be a significant advance to provide a catheter balloon, or other medical device component, with improved performance and bondability.

SUMMARY OF THE INVENTION

This invention is directed to a balloon catheter and a method of making a balloon catheter, having a balloon with a first layer and a second layer, the first layer having at least one impregnated section impregnated with a polymeric material compatible with a polymeric material forming the catheter shaft. At least a portion of the impregnated section is fusion bonded to the shaft. In a presently preferred embodiment, the impregnated section is adjacent to a section of the first layer which is not impregnated with the compatible polymeric material. The impregnated section provides improved bonding of the balloon to the catheter shaft while minimizing the effect of the bond on catheter performance characteristics such as profile and flexibility.

A balloon catheter of the invention generally comprises an elongated shaft having a proximal end, a distal end, at least one lumen, and at least a surface formed of a polymeric material, and a balloon on a distal shaft section with an interior in fluid communication with the at least one lumen of the shaft. The balloon has a proximal skirt section bonded to the shaft, a distal skirt section bonded to the shaft, and first and second layers extending from the proximal skirt section to the distal skirt section. At least one of the skirt sections of the balloon is formed at least in part by the impregnated section of the first layer fusion bonded to the shaft. In a presently preferred embodiment, the first layer has a proximal impregnated section at least in part forming the proximal skirt section, and a distal impregnated section at least in part forming the distal skirt section. Preferably, end sections of the second layer are also bonded to the shaft, although they are not impregnated. Thus, the proximal and distal skirt sections of the balloon are preferably formed in part by the end sections of the second layer, and in part by the impregnated sections of the first layer of the balloon. The proximal and distal impregnated sections of the first layer are preferably adjacent to one or more sections of the first layer which are not impregnated with the polymeric material impregnated in the impregnated sections.

The impregnated section of the first layer of the balloon is impregnated with a polymeric material which is compatible with the polymeric material of the shaft, so that the impregnated section improves fusion bonding between the first layer of the balloon and the shaft. In one embodiment, the bond between the shaft and the proximal and distal skirt sections of the balloon is sufficiently strong to withstand balloon inflation pressures of about 90 to about 300 psi without failing (i.e., without rupturing or ballooning at the site of the bond or allowing inflation fluid to seep through the ePTFE layer of the balloon). The term compatible should be understood to refer to polymeric materials which are fusion bondable together. More specifically, compatible polymeric materials bond together by chemical bonds (i.e., covalent or hydrogen bonds), and preferably are thermodynamically miscible together. In one embodiment, the polymeric material impregnated in the first layer impregnated section ("the compatible polymeric material") is the same polymeric material as the shaft polymeric material. For example, in one embodiment, the compatible polymeric material and the shaft polymeric material are the same polymer and are selected from the group consisting of Nylon 12, polyether block amide (PEBAX), polyurethanes, and copolymers thereof, and acrylonitrile butadiene styrene (ABS). However, the compatible polymeric material is not necessarily the same polymer as the shaft polymeric material. In one embodiment, the compatible polymeric material is from the same family or class of polymeric materials as the shaft polymeric material, so that the polymers will covalently bond together. For example, in one embodiment, the compatible polymeric material is a nylon and the shaft polymeric material is PEBAX, and thus the polymers are both from the family of polymers known as polyamides. In another embodiment, the compatible polymeric material and the shaft polymeric material are from different polymer families, but will hydrogen bond together, such as, for example, polyurethane and PEBAX, or nylon and polyurethane.

In one embodiment, the compatible polymeric material is soluble in an alcohol, unlike polymers such as nylon 12 which are not soluble in alcohol. For example, ELVAMIDE, available from Dupont, is a thermoplastic polyamide soluble in alcohols including methanol, ethanol, 2-propanol, and a mixture of these with water. Such alcohols are readily available, and typically have a higher vapor pressure, lower toxicity, and lower cost than organic solvents commonly used for polymers such as nylon 12, and thus improve the manufacturability of the balloon catheter.

Preferably, the one or more impregnated sections of the balloon first layer are located only at the regions of the balloon skirt sections. Thus, the impregnated sections typically have a shorter length than the length of the first layer which is not impregnated with the compatible polymeric material. The combined length of the proximal and distal impregnated sections of first layer is typically about 10 to about 50% of the length of the first layer. In one embodiment, the impregnated section(s) of the first layer has a length approximately equal to the length of the section(s) of the first layer bonded to the shaft. Consequently, the impregnated section(s) has minimal effect on balloon performance characteristics such as compliance.

The first layer is formed of a porous polymeric material which in one embodiment is selected from the group consisting of expanded polytetrafluoroethylene (ePTFE), an expanded ultra high molecular weight polyolefin such as expanded ultra high molecular weight polyethylene, porous polyethylene, porous polypropylene, and porous polyurethane. In one embodiment, the porous material has a node and fibril microstructure. The node and fibril microstructure, when present, is produced in the material using conventional methods. ePTFE and expanded ultra high molecular weight polyethylene typically have a node and fibril microstructure, and are not melt extrudable. However, a variety of suitable polymeric materials can be used in the method of the invention including conventional catheter balloon materials which are melt extrudable. Preferably, ePTFE is formed into a balloon layer by bonding wrapped layers of the polymeric material together to form a tubular member, and not by conventional balloon blow molding. Although discussed primarily in terms of the embodiment in which the first layer of the balloon comprises ePTFE, it should be understood that a variety of suitable polymers may be used for the first layer.

In a presently preferred embodiment, the first layer is an outer layer relative to the second layer, although the first layer may alternatively be an inner layer relative to the second layer. In one embodiment, the outer (e.g., first) layer extends beyond the ends of the inner (e.g., second) layer. Specifically, in one embodiment, the first layer has a proximal end section and a distal end section, extending beyond the inner layer and in contact with and bonded to the shaft. The impregnated sections of the outer layer extend along at least part of the end sections of the outer layer which are in contact with and bonded to the shaft. Although discussed primarily in terms of the embodiment in which the first layer formed of ePTFE or other porous polymer is the outer layer of the balloon, it should be understood that the balloon can have one or more ePTFE layers forming an outer, inner, or middle layer of the balloon.

A balloon catheter of the invention can be configured for use in a variety of applications including coronary and peripheral dilatation, stent delivery, drug delivery, and the like.

A method of making a balloon catheter which embodies features of the invention generally includes positioning a distal section of a catheter shaft within a first tube forming a tubular inner layer of the balloon, the tubular inner layer being formed of an elastomeric polymer and having a proximal end section, and a distal end section. A second tube forming a tubular outer layer of the balloon, formed of a porous polymeric material, is positioned on an outer surface of the tubular inner layer, with a proximal end section and a distal end section of the tubular outer layer in contact with the catheter shaft and having at least a portion impregnated with a polymeric material compatible with the polymeric material of the shaft and adjacent to a section of the outer layer which is not impregnated with the compatible polymeric material. The inner tubular layer is preferably bonded to the shaft before the outer tubular layer is positioned therearound, although it may alternatively be bonded to the shaft during the fusion bonding of the outer layer to the shaft. Thus, in one embodiment, prior to positioning the outer layer around the inner layer, heat is applied at the proximal and distal end sections of the inner tubular layer, to melt the shaft polymeric material and the polymeric material of the inner tubular layer and fusion bond the proximal and distal end sections to the catheter shaft. Then the outer tubular layer is positioned therearound and heat similarly applied thereto to melt the shaft polymeric material and the compatible polymeric material and fusion bond the proximal and distal end sections to the catheter shaft.

Although discussed in terms of a preferred embodiment in which the fusion bond between the balloon and shaft is a heat fusion bond, the fusion bond may alternatively be a solvent fusion bond. In the heat fusion bonding, the polymeric materials are heated to an elevated temperature at or around the melting temperature(s) of the polymeric materials, so that the polymers melt together. The elevated temperature is typically within about 120° C. to about 250° C. of the melting temperature of the polymers. For example, in one preferred embodiment, the elevated temperature is about 170° C. or more for PEBAX, and about 120° C. or more for polyurethane. Alternatively, the polymeric materials are solvent fusion bonded together by solubilizing the polymers together in a solvent and evaporating the solvent.

The balloon catheter of the invention has an improved bond between the balloon and the catheter shaft due to the impregnated section of the first layer of the balloon. The impregnated section provides a strong fusion bond, without requiring adhesives or polymer sleeves, and thus minimizes disadvantageously large increases in stiffness and profile at the bond. Moreover, the balloon of the invention has a improved manufacturability. These and other advantages of the invention will become more apparent from the following detailed description and accompanying exemplary figures.

BRIEF DESCRIPTION OF THE DRAWINGS

FIG. 1 is an elevational view, partially in section, of a stent delivery balloon catheter embodying features of the invention.

FIG. 1A is an enlarged sectional view of the catheter shown in FIG. 1, taken within area 1A.

FIG. 2 is a transverse cross sectional view of the balloon catheter shown in FIG. 1, taken along line 2-2.

FIG. 3 is a transverse cross sectional view of the balloon catheter shown in FIG. 1, taken along line 3-3.

FIG. 4 is a transverse cross sectional view of the balloon catheter shown in FIG. 1, taken along line 4-4.

FIG. 5 illustrates the balloon catheter of FIG. 1, with the balloon in an inflated configuration to expand the stent within the patient's body lumen.

DETAILED DESCRIPTION OF THE INVENTION

FIG. 1 illustrates an over-the-wire type stent delivery balloon catheter 10 embodying features of the invention. Catheter 10 generally comprises an elongated catheter shaft 12 having an outer tubular member 14 and an inner tubular member 16. Inner tubular member 16 defines a guidewire lumen 18 configured to slidingly receive a guidewire 20, and the coaxial relationship between outer tubular member 14 and inner tubular member 16 defines annular inflation lumen 22, as best shown in FIG. 2 illustrating a transverse cross section of the distal end of the catheter shown in FIG. 1, taken along line 2-2. An inflatable balloon 24 disposed on a distal section of catheter shaft 12 has a proximal skirt section 25 sealingly secured to the distal end of outer tubular member 14 and a distal skirt section 26 sealingly secured to the distal end of inner tubular member 16, so that the balloon interior is in fluid communication with inflation lumen 22. An adapter 36 at the proximal end of catheter shaft 12 is configured to provide access to guidewire lumen 18, and to direct inflation fluid through arm 38 into inflation lumen 22. In the embodiment illustrated in FIG. 1, the balloon 24 is illustrated in a noninflated configuration, with an expandable stent 30 mounted on the working length of the uninflated balloon 24 for delivery and deployment within a patient's body lumen 32. In the embodiment illustrated in FIG. 1, the uninflated balloon 24 has a wingless, low profile configuration prior to complete inflation of the balloon. The distal end of catheter may be advanced to a desired region of the patient's body lumen 32 in a conventional manner, the balloon 24 inflated to expand stent 30, and the balloon deflated, to implant the stent 30 in the body lumen 32.

Balloon 24 has an outer layer 33 and an inner layer 34, extending from the proximal skirt section 25 to the distal skirt section 26 of the balloon. In the embodiment illustrated in FIG. 1, the outer layer 33 of the balloon 24 has a proximal impregnated section 27 bonded to the outer tubular member 14, and a distal impregnated section 28 bonded to the inner tubular member 16. The impregnated sections 27, 28 of the outer layer 33, together with end sections of the inner layer 34 bonded to the shaft 12, form the proximal and distal skirt sections 25, 26, respectively. Thus, in the embodiment illustrated in FIG. 1, the proximal skirt section 25 is formed at least in part by a proximal end section of the inner layer 34 which is bonded to the shaft outer tubular member 14 and by the proximal impregnated section 27 of the outer layer 33 which extends beyond the inner layer 34 and which is bonded to the shaft outer tubular member 14. Similarly, the distal skirt section 26 is formed at least in part by a distal end section of the inner layer 34 which is bonded to the shaft inner tubular member 16 and by the distal impregnated section 28 of the outer layer 33 which extends beyond the inner layer 34 and which is bonded to the shaft inner tubular member 16.

The length of the sections of each layer 33 and 34 of the balloon 24 secured to the shaft to form the proximal and distal skirt sections 25, 26 are preferably minimized. Thus, the proximal and distal skirt sections 25, 26 preferably have a length about equal to the minimal length required to provide a suitably strong bond between the balloon 24 and the shaft 12. The length of the proximal end section of the inner layer 34 bonded to the outer tubular member 14 is about 1 to about 5 mm, and the length of the proximal end section of the outer layer 33 extending beyond the inner layer 34 and bonded to the outer tubular member 14 is typically about 1 mm to about 4 mm, preferably about 1 mm to about 2 mm. Similarly, length of the distal end section of the inner layer 34 bonded to the inner tubular member 16 is about 1 to about 5 mm, and the length of the distal end section of the outer layer 33 extending beyond the inner layer 34 and bonded to the inner tubular member 16 is typically about 1 mm to about 4 mm, preferably about 1 mm to about 2 mm.

The impregnated sections 27, 28 of the outer layer 33 of the balloon 24 are impregnated with a polymeric material 40 compatible with the polymeric material of the outer and inner tubular members 14, 16. Although the distal impregnated section 28 is impregnated with the same polymer 40 as the proximal impregnated section 27 in the embodiment of FIG. 1, in an alternative embodiment (not shown), the distal impregnated section 28 is impregnated with a different polymer than the polymer 40 impregnated in the proximal impregnated section 27. In the embodiment illustrated in FIG. 1, the outer and inner tubular members 14, 16 are each formed of a single-layered, uniform polymeric member. However, it should be understood that in alternative embodiments, one or both of the outer and inner tubular members 14, 16 may be a multilayered or blended polymeric member. The compatible polymeric material 40 is not necessarily compatible with all the polymers forming parts of the shaft. Thus, the shaft has at least a surface formed of a polymeric material, and the compatible polymeric material 40 is compatible with said polymeric material forming the surface of the outer and inner tubular members 14,16 to which the impregnated section is bonded.

The compatible polymer 40 impregnated in sections 27, 28 of outer layer 33 facilitates fusion bonding the outer layer 33 of the balloon 24 to the shaft 12. In one embodiment, the compatible polymer 40 is the same polymer as the polymeric material of the shaft 12, for superior fusion bonding, and is selected from the group consisting of nylon, PEBAX, and polyurethanes. In another embodiment, the compatible polymeric material and the shaft polymeric from the same polymer family, and are selected from the group consisting of polyamides (e.g., nylon 12, PEBAX, and Elvamide), and polyurethanes (e.g., Pellethane and Tecothane). The compatible polymeric material 40 may be the same polymer as, or a different polymer than, the polymeric material forming the inner layer 34 of the balloon. In a presently preferred embodiment, the inner layer is formed of a polymeric material compatible with the polymeric material of the shaft 12, to facilitate fusion bonding of layer 34 to the shaft 12.

Preferably, the outer layer 33 and inner layer 34 of the balloon 24 are fusion bonded directly to the outer tubular member 14 and the inner tubular member 16 of the shaft 12, without an adhesive or separate polymer layer between the layers 33, 34 and the shaft 12. Alternatively, in one embodiment, an adhesive or a separate polymer member is used to facilitate bonding at least the inner layer 34 to the shaft 12. Conventional adhesives such as light-cured (e.g., Dymax 204) and cyanoacrylates (e.g., Loctite 4011) may be used to bond inner layer 34 to the shaft 12. It should be understood that the surface of outer layer 33 in contact with and directly fusion bonded to the shaft 12 may have been provided with surface treatments or other pretreatments, for enhancing the bondability of materials such as ePTFE.

In the embodiment illustrated in FIG. 1, the impregnated sections 27, 28 extend only along the portions of the outer layer 33 which are in contact with and directly bonded to the shaft. Thus, the distal end of the proximal impregnated section 27 is located at the proximal end of the inner layer 34, and the proximal end of the distal impregnated section 28 is located at the distal end of the inner layer 34. In an alternative embodiment (not shown), the distal end of the proximal impregnated section 27 is located distal to the portion of the outer layer 33 in contact with and directly fusion bonded to the outer tubular member 14, and the proximal end of the distal impregnated section 28 is located proximal to the portion of the outer layer 33 in contact with an directly fusion bonded to the inner tubular member 16. Preferably, the impregnated sections 27, 28 of the outer layer 33 of the balloon 24 do not extend into a portion of the outer layer 33 located between the proximal and distal skirt sections 25, 26 of the balloon.

The impregnated sections 27, 28 of the outer layer 33 are adjacent to a section of the outer layer 33 which is not impregnated with the compatible polymer 40. Thus, the impregnated sections 27, 28 of the outer layer 33 do not extend the entire length of the outer layer 33, and preferably have a combined length which is less than the length of the section of the first layer which is not impregnated with the compatible polymeric material 40. The section of the outer layer 33 which is not impregnated with the compatible polymer 40 includes the central working length of the balloon 24 on which the stent 30 is mounted. In the embodiment illustrated in FIG. 1, the central section of the outer layer 33 is not impregnated with the compatible polymer 40 or with another polymer, apart from being bonded to inner layer 34 which may at least partially fill some of the pores of the porous outer layer 33. However, it should be understood that all or part of the sections of the outer layer 33 which are not impregnated with compatible polymer 40 may be impregnated with a polymeric material different than the compatible polymer 40.

The length of the proximal impregnated section 27 of outer layer 33 is typically about 5 to about 20%, preferably about 5 to about 15% of the length of the outer layer 33, and the length of the distal impregnated section 28 of outer layer 33 is typically about 5 to about 20%, preferably about 5 to about 15% of the length of the outer layer 33. Specifically, in one embodiment, the length of the proximal impregnated section 27 of outer layer 33 is about 1 to about 4 mm, and the length of the distal impregnated section 28 of outer layer 33 is about 1 to about 4 mm, for a balloon 24 having a length of about 8 to about 60 mm and a nominal outer diameter of about 2 to about 18 mm.

In a presently preferred embodiment, the outer layer 33 comprises a porous polymeric material, and preferably a microporous polymeric material having a node and fibril microstructure, such as ePTFE, and the inner layer 34 is formed of a polymeric material preferably different from the polymeric material of the outer layer 33. Preferably, the length of outer layer 33 in contact with inner layer 34 is bonded thereto, and preferably by heat fusion bonding. Inner layer 34 limits or prevents leakage of inflation fluid through the microporous ePTFE to allow for inflation of the balloon 24, and is preferably an elastomeric material to facilitate deflation of the balloon 24 to a low profile deflated configuration. The elastomeric material forming layer 34 may consist of a separate layer which neither fills the pores nor disturbs the node and fibril structure of the ePTFE layer 33, or it may at least partially fill the pores of the ePTFE layer 33. The inner layer 34 is preferably formed of an elastomeric material, including dienes, polyurethanes, silicone rubbers, polyamide block copolymers, and the like.

The ePTFE layer 33 is formed according to conventional methods, in which a sheet of ePTFE polymeric material is wrapped with overlapping or abutting edges to form a tubular body and then heated to fuse the wrapped material together. The sheet of polymeric material preferably has the desired microstructure (e.g., porous and/or node and fibril) before being wrapped on the mandrel. The sheet of ePTFE polymeric material is wrapped spirally along a length of the mandrel, or by folding the sheet around the circumference of the mandrel so that the longitudinal edges of the sheet extend in a substantially straight line along the length of the mandrel, to form one or more layers, and preferably about two to about five layers, of wrapped material. The multiple layers of ePTFE are typically heated to fuse the layers together. The tube of ePTFE polymeric material is typically further processed by being stretched, sintered, compacted, and sintered again, to provide the desired properties such as the desired dimension, and dimensional stability (i.e., to minimize changes in length occurring during inflation of the balloon). The completed ePTFE layer 33 is then bonded to or otherwise combined with elastomeric liner 34 which in one embodiment is already secured to the catheter shaft 12.

In a method of making a balloon catheter having a balloon with an inner layer and an outer layer, a distal section of catheter shaft is positioned within a tubular inner layer 34 of the balloon, so that the distal end of the outer tubular member 14 and the distal end of the inner tubular member 16 of shaft 12 are within the proximal and distal end sections of the inner layer 34, respectively. Heat is applied at the proximal and distal end sections of the inner tubular layer 34, to melt the polymeric material of the shaft 12 and the polymeric material of the inner tubular layer 34 at least at the interface thereof, and fusion bond the proximal and distal end sections of the inner tubular layer 34 of the balloon 24 to the outer and inner tubular members 14, 16, respectively. Specifically, in one embodiment, an inner tubular layer 34 formed of polyurethanes (e.g., Pursil, and Tecoflex) or dienes such as synthetic diene rubber, and a shaft having at least an outer layer formed of polyamides or polyurethanes, with shrink tubing therearound, are heated by a laser to a temperature at or above the melting temperature of the polymers, and specifically to a temperature of about 120 to about 250° C., and more specifically to a temperature of greater than or equal to about 120° C. for a polyurethane shaft and to a temperature of greater than or equal to about 170° C. for a PEBAX shaft.

A tubular outer layer 33 of the balloon 24, formed of a porous polymeric material such as for example ePTFE, is positioned on an outer surface of the tubular inner layer 34, with a proximal impregnated section 27 of the tubular outer layer located proximal to the proximal end section of the tubular inner layer 34 and in contact with the outer tubular member 14, and with a distal impregnated section 28 of the tubular outer layer 33 located distal to the distal end section of the tubular inner layer 34 and in contact with the inner tubular member 16.

The proximal and the distal impregnated end sections 27, 28 of the tubular outer layer 33 of the balloon are impregnated with a polymeric material compatible with the polymeric material of the shaft 12. Specifically, a solution of the compatible polymeric material is applied to the end sections of the outer layer 33 before or after the tubular outer layer 33 is positioned around the balloon inner layer 34 and the catheter shaft 12. In one embodiment, with the outer layer in place around the inner layer of the balloon, compatible polymer solution is applied, as for example by dipping, pouring, or spraying, on an outer surface of the end sections of the outer layer, so that the solution fills the pores of the porous polymeric material at the end sections of outer layer 33. Alternatively, the end sections of the outer layer 33 of the balloon 24 are impregnated with the compatible polymeric material solution before being placed in position around the balloon inner layer 34 and the shaft 12, as for example, by dipping the end sections of the outer layer 33 into the solution. A sufficient amount of solution is applied to saturate the end sections of the outer layer of the balloon, so that the solution fills the pores of the porous outer layer 33 and at least some compatible polymer is at the inner surface of the outer layer after evaporation of the solvent. In one embodiment, the amount of solution in the porous outer layer 33 is about 1 to about 20% by weight, for a porous outer layer 33 having a porosity prior to impregnation of about 80% to about 90%. In one embodiment, after impregnation, the porosity is about 65% to about 75%. The concentration of the compatible polymeric material solution is about 5 to about 40%, and preferably about 5 to about 15%, depending on the compatible polymer and the nature of the polymer forming the outer layer. In the embodiment in which the compatible polymeric material solution comprises a common solvent such as an alcohol such as methanol or ethanol, the concentration of the compatible polymeric material solution is about 5 to about 40%, and preferably about 5 to about 15%. After evaporation of the solvent, the amount of compatible polymer impregnated in the outer layer 33 is typically about 1 to about 20% by weight, preferably about 1 to about 10% by weight of the outer layer 33.

The proximal and distal impregnated sections 27, 28 of the tubular outer layer 33 of the balloon 24 are adjacent to one or more sections of the outer layer 33 which are not impregnated with the compatible polymeric material. The compatible polymer solution is prevented or inhibited from migrating beyond the end sections of the outer layer of the balloon and into the adjacent sections of the outer layer of the balloon by a method involving masking the areas. In one embodiment, at least the majority of the compatible polymer solution remains where applied at the end sections of the outer layer 33. In one embodiment, some of the solution may migrate beyond the end sections of the outer layer of the balloon into the adjacent sections of the outer layer 33.

The proximal and distal impregnated sections 27, 28 of the tubular outer layer 33 of the balloon 24 are heated as set forth above, to melt the shaft polymeric material 12 and the compatible polymeric material 40 impregnated in the outer layer 33, and thereby fusion bond the proximal and distal end sections of the outer layer 33 to the catheter shaft 12. Specifically, the shaft and the impregnated section of an outer tubular layer formed of ePTFE impregnated with a polymer such as for example polyamides (e.g., Elvamide) and polyurethanes (e.g., Pellethane and Tecothane), with shrink tubing therearound, are heated by a laser, to a temperature at or above the melting temperature of the polymers, and specifically to a temperature of about 120° C. to about 250° C., to fusion bond the outer layer of the balloon to the shaft.

The resulting balloon catheter preferably has a rupture pressure of at least about 20 atm. During a medical procedure, the balloon is typically inflated to a working pressure of about 6 atm to about 25 atm, preferably about 6 atm to about 20 atm. The balloon is inflatable within the working pressure range without the skirt sections 25, 26 of the balloon 24 failing.

The dimensions of catheter 10 are determined largely by the size of the balloon and guidewire to be employed, the catheter type, and the size of the artery or other body lumen through which the catheter must pass or the size of the stent being delivered. Typically, the outer tubular member 14 has an outer diameter of about 0.025 to about 0.04 inch (0.064 to 0.10 cm), usually about 0.037 inch (0.094 cm), and the wall thickness of the outer tubular member 14 can vary from about 0.002 to about 0.008 inch (0.0051 to 0.02 cm), typically about 0.003 to 0.005 inch (0.0076 to 0.013 cm). The inner tubular member 16 typically has an inner diameter of about 0.01 to about 0.018 inch (0.025 to 0.046 cm), usually about 0.016 inch (0.04 cm), and a wall thickness of about 0.004 to about 0.008 inch (0.01 to 0.02 cm). The overall length of the catheter 10 may range from about 100 to about 150 cm, and is typically about 143 cm. Preferably, balloon 24 has a length about 0.5 cm to about 6 cm, and an inflated working diameter of about 2 to about 10 mm.

Inner tubular member 16 and outer tubular member 14 can be formed by conventional techniques, for example by extruding and necking materials already found useful in intravascular catheters such a polyethylene, polyvinyl chloride, polyesters, polyamides, polyimides, polyurethanes, and composite materials. The various components may be joined using conventional bonding methods such as by fusion bonding or use of adhesives. Although the shaft is illustrated as having an inner and outer tubular member, a variety of suitable shaft configurations may be used including a dual lumen extruded shaft having a side-by-side lumens extruded therein. Similarly, although the embodiment illustrated in FIG. 1 is an over-the-wire stent delivery catheter, balloons of this invention may also be used with other types of intravascular catheters, such as rapid exchange dilatation catheters. Rapid exchange catheters generally comprise a distal guidewire port in a distal end of the catheter, a proximal guidewire port in a distal shaft section distal of the proximal end of the shaft and typically spaced a substantial distance from the proximal end of the catheter, and a short guidewire lumen extending between the proximal and distal guidewire ports in the distal section of the catheter.

While the present invention is described herein in terms of certain preferred embodiments, those skilled in the art will recognize that various modifications and improvements may be made to the invention without departing from the scope thereof. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

What is claimed:

1. A method of making a balloon catheter, comprising:
   a) positioning a distal section of a catheter shaft having at least a surface formed of a polymeric material within a first tube forming a tubular inner layer of a balloon, the tubular inner layer having a proximal end section, and a distal end section and being formed of an elastomeric polymeric material;
   b) applying heat at the proximal and distal end sections of the inner tubular layer, to melt the shaft polymeric material and the polymeric material of the inner layer and fusion bond the proximal and distal end sections to the catheter shaft;
   c) positioning a second tube forming a tubular outer layer of the balloon on an outer surface of the tubular inner layer, with a proximal end section and distal end section of the tubular outer layer in contact with the catheter shaft, the proximal and the distal end sections of the tubular outer layer having at least a portion impregnated with a polymeric material compatible with the polymeric material of the shaft and adjacent to a section of the outer layer which is not impregnated with the compatible polymeric material, wherein the sections having at least a portion thereof impregnated with the polymeric material are shorter along a length of the outer layer than the section that is not impregnated with the polymeric material; and
   d) applying heat at the proximal and distal end sections of the outer tubular layer, to melt the shaft polymeric material and the impregnated compatible polymeric material and fusion bond the impregnated portions of the proximal and distal end sections of the outer layer to the catheter shaft.

2. The method of claim 1 wherein the impregnated compatible polymeric material is different from a polymeric material forming the inner layer of the balloon, and including forming the impregnated portions of the outer layer by applying a solution of the compatible polymeric material to a surface of the second tube.

3. The method of claim 1 wherein (d) comprises applying the heat only along the proximal and distal end sections of the outer layer, and wherein the impregnated portions of the outer layer have a length approximately equal to the length of the sections of the outer layer bonded to the shaft such that the one or more impregnated portions of the balloon outer layer do not extend along any section of an inflatable length of the balloon.

4. The method of claim 1 wherein the distal end section impregnated portion is impregnated with a different polymer than the proximal end section impregnated portion.

5. The method of claim 1 wherein an adhesive or a separate polymer member is bonding the inner layer to the shaft.

6. The method of claim 1 wherein the compatible polymeric material in the impregnated section of the outer layer of the balloon is soluble in alcohol such that a solvent forming the solution applied to the second tube is an alcohol, and including evaporating the alcohol solvent to leave the compatible polymeric material impregnated in the outer layer.

7. A method of making a balloon catheter, comprising:
   a) positioning a distal section of a catheter shaft having at least a surface formed of a polymeric material within a first tube forming a tubular inner layer of a balloon, the tubular inner layer having a proximal end section, and a distal end section and being formed of an elastomeric polymeric material;
   b) positioning a second tube forming a tubular outer layer of the balloon on an outer surface of the tubular inner layer, with a proximal end section and a distal end section of the tubular outer layer in contact with the catheter shaft;
   c) impregnating the proximal and the distal end sections of the tubular outer layer with a polymeric material fusible with the polymeric material of the shaft by applying a solution of the fusible polymeric material to a surface of the outer layer to form impregnated portions adjacent to a section of the outer layer which is not impregnated with the fusible polymeric material, wherein the solution is applied along lengths of the outer layer which are shorter than the section of the outer layer which is not impregnated; and
   d) impregnated portions of the outer layer and the inner layer to the catheter shaft such that the resulting balloon has a proximal skirt section and a distal skirt section fusion bonded to the shaft and an inflatable section therebetween with an interior in fluid communication with an inflation lumen of the catheter shaft, and wherein the outer layer and the inner layer extend along the inflatable section from the proximal to the distal skirt section of the balloon.

8. The method of claim 7 wherein the fusion bonding of the outer layer to the catheter shaft comprises heat fusion bonding the outer layer and the shaft together.

9. The method of claim 7 wherein the fusion bonding of the outer layer to the catheter shaft comprises solvent fusion bonding the outer layer and shaft together by solubilizing polymers thereof together in a solvent and evaporating the solvent.

10. The method of claim 7 wherein the solution is applied to an outer surface of the tubular outer layer after the outer layer is placed on the tubular inner layer.

11. The method of claim 7 wherein the impregnated compatible polymeric material is different from a polymeric material forming the inner layer of the balloon, and including bonding the balloon inner layer to the balloon outer layer.

12. A method of making a balloon catheter having a balloon bonded to a shaft, the shaft having at least a surface formed of a polymeric material, comprising:
   a) impregnating a proximal and a distal end portion of a porous polymeric tube with a polymeric material fusible with the polymeric material of the shaft by applying a solution of the fusible polymeric material to a surface of the tube, to form impregnated proximal and distal end portions adjacent to a section of the tube which is not impregnated with the fusible polymeric material, wherein the solution is applied along lengths of the tube which are shorter than the section of the outer layer which is not impregnated with the compatible polymeric material; and
   b) impregnated portions of the tube to the catheter shaft to form an outer tubular layer of the balloon which is positioned on an outer surface of an inner tubular layer of the balloon and which has the proximal and distal impregnated end portions of outer tubular layer in contact with and bonded to the catheter shaft, such that the balloon has a proximal and a distal skirt section fusion bonded to the shaft and an inflatable section therebetween with an interior in fluid communication with an inflation lumen of the catheter shaft, and wherein the outer layer and the inner layer extend along the inflatable section from the proximal to the distal skirt section of the balloon.

* * * * *

UNITED STATES PATENT AND TRADEMARK OFFICE
CERTIFICATE OF CORRECTION

PATENT NO. : 7,981,244 B2  
APPLICATION NO. : 11/585071  
DATED : July 19, 2011  
INVENTOR(S) : Florencia Lim et al.

Page 1 of 1

It is certified that error appears in the above-identified patent and that said Letters Patent is hereby corrected as shown below:

Column 12, line 14, between "d)" and "impregnated" insert --fusion bonding the--.
line 52, between "b)" and "impregnated" insert --fusion bonding the--.

Signed and Sealed this  
Thirty-first Day of July, 2012

David J. Kappos  
*Director of the United States Patent and Trademark Office*